(12) United States Patent
Kim et al.

(10) Patent No.: US 7,745,218 B2
(45) Date of Patent: Jun. 29, 2010

(54) GENOME MINIMIZATION BY TN5-COUPLED CRE/LOXP EXCISION SYSTEM

(75) Inventors: Sun-Chang Kim, Daejeon (KR); Byung-Jo Yu, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 1710 days.

(21) Appl. No.: 10/505,328

(22) PCT Filed: Oct. 31, 2002

(86) PCT No.: PCT/KR02/02033

§ 371 (c)(1),
(2), (4) Date: Aug. 23, 2004

(87) PCT Pub. No.: WO03/070955

PCT Pub. Date: Aug. 28, 2003

(65) Prior Publication Data

US 2009/0104682 A1 Apr. 23, 2009

(30) Foreign Application Priority Data

Feb. 22, 2002 (KR) .................... 10-2002-0009647

(51) Int. Cl.
*C12N 15/00* (2006.01)
*C12N 15/70* (2006.01)
*C12N 15/74* (2006.01)
*C07H 21/04* (2006.01)

(52) U.S. Cl. .................... 435/473; 435/320.1; 435/440; 435/471; 536/23.1

(58) Field of Classification Search .................... None
See application file for complete search history.

(56) References Cited

FOREIGN PATENT DOCUMENTS

WO  WO 9810077 A1 * 3/1998
WO  WO 0118222 A1 * 3/2001

OTHER PUBLICATIONS

Posfai et al. In vivo excision and amplification of large segments of the *Escherichia coli* genome. Nucleic Acids Research, vol. 22, No. 12, pp. 2392-2398, 1994.*
Yoon et al. Cre/loxP-mediated excision and amplification of large segments of the *Escherichia coli* genome. Genetic Analysis: Biomolecular Engineering, vol. 14, pp. 89-95, 1998.*
Bloch et al. Purification of *Escherichia coli* chromosomal segments without cloning. Biochemical and Biophysical Research Communications, vol. 223, pp. 104-111, 1996.*
Kilbride et al. Topological selectivity of a hybrid site-specific recombination system with elements from Tn3 res/resolvase and bacteriophage P1 loxP/Cre. Journal of Molecular Biology, vol. 289, pp. 1219-1230, 1999.*
"Isolating Large Nested Deletions in Bacterial And P1 Artificial Chromosomes by in vivo P1 Packaging of Products of Cre-Catalysed Recombination Between the Endogenous and a Transposed *loxP* site"; Pradeep Chatterjee et al.; *Nucleic Acids Research*, 1997, vol. 25, No. 11.
"Genetic Analysis of the Lytic Replicon of Bacteriophage P1", Nat Sternberg et al., *Journal of Molecular Biology*, (1989), 207, pp. 111-133.
Chatterjee, P., et al., "Analysis of a Clonal Selection Event During Transposon-Mediated Nested-Deletion Formation in Rare BAC and PAC Clones," Analytical Biochemistry, vol. 285, pp. 121-126 (2000).
Coren, J., at al., "Construction of a PAC Vector System for the Propagation of Genomic DNA in Bacterial and Mammalian Cells and Subsequent Generation of Nested Deletions in Individual Library Members," Gene, vol. 264, No. 1, pp. 11-18 (2001).
Gilmore, R., et al., "Using PAC Nested Deletions to Order Contigs and Microsatellite Markers at the High Repetitive Sequence Containing Npr3 Gene Locus," Gene, vol. 275, pp. 65-72 (2001).
Hoekstra, M., et al., "A Tn3 Derivative That Can Be Used to Make Short In-Frame Insertions Within Genes," Proc. Natl. Acad. Sci., USA, vol. 88, pp. 5457-5461 (1991).
Wild., J., et al., "Targeting and Retrofitting Pre-Existing Libraries of Transposon Insertions with FRT and oriV Elements for In-Vivo Generation of Large Quantities of Any Genomic Fragment," Gene. vol. 223, pp. 55-66 (1998).
Supplementary European Search Report of European Application No. 02790956.3 dated May 17, 2005.
Yu, B., et al., "Minimization of the *Escherichia coli* Genome Using a Tn5-Targeted Cre/*loxP* Excision System," Nature Biotechnology, vol. 20, pp. 1018-1023 (2002).
Ayres, E., et al., "Precise Deletions in Large Bacterial Genomes By Vector-Mediated Excision (VEX) The *trfA* Gene of Promiscuous Plasmid RK2 is Essential for Replication in Several Gram-negative Hosts," Journal of Molecular Biology, vol. 230, pp. 174-185 (1993).
Tsuda, M., "Use of a Transposon-Encoded Site-Specific Resolution System for Construction of Large and Defined Deletion Mutations in Bacterial Chromosome," Gene, vol. 207, pp. 33-41 (1998).
Delneri, D., et al., "Exploring Redundancy in the Yeast Genome: An Improved Strategy for Use of the *cre-loxP* System," Gene, vol. 252, pp. 127-135 (2000).
Siegel, R., et al., "Using an in Vivo Phagemid System to Identify Non-Compatible *loxP* Sequences," FEBS Letters, No. 499, pp. 147-153 (2001).
Koob, M., et al., "Minimizing the Genome of *Escherichia Coli* Motivation and Strategy," Annals New York Academy of Sciences, vol. 745, pp. 1-3 (1994).

* cited by examiner

*Primary Examiner*—Jennifer Dunston
(74) *Attorney, Agent, or Firm*—Howrey LLP

(57) ABSTRACT

Disclosed is a method for developing novel strains deleted specific chromosome sites, using transposon and Cre/loxP site-specific recombination by Cre expression vector, wherein the transposon comprises a selectable marker and loxP site. The method comprises the steps of: (1) preparing a transposon comprising a selectable marker and loxP site; (2) inserting the transposon into an optional position of microbial chromosome, and determining the inserted site; (3) integrating two transposons comprising a different selectable marker to one chromosome; (4) deleting a chromosomal site between the two lox sites by introducing a Cre expression vector into the chromosome of step (3); and (5) repeating steps (3 and 4) for the mutant deleted a part of chromosome, to shorten the chromosome of mutant gradually.

6 Claims, 6 Drawing Sheets

GENOME MINIMIZATION BY TN5-COUPLED CRE/LOXP EXCISION SYSTEM

TECHNICAL FIELD

The present invention relates to strains deleted specific chromosome sites, using transposon with loxP site and Cre/loxP site-specific recombination, and the construction method thereof. More particularly, the present invention relates to a method for constructing novel strains deleted specific chromosome sites, by Cre/loxP site-specific recombination using a transposon comprising a selectable marker and loxP site, and a Cre expression vector.

BACKGROUND ART

Even though the technology to delete specific chromosome sites of *E. coli* by using Cre/loxP site specific recombination is generally known, it has been required to prepare targeting vector and perform PCR (polymerase chain reaction) in every experiment to delete specific chromosome sites in the conventional methods. The random transposition of transposon into the chromosome is also well known. However, it has not been reported that chromosome sites of microorganism can be deleted using transposon together with Cre/loxP site-specific recombination

DETAILED DESCRIPTION OF THE INVENTION

The present invention relates to a method of deleting specific chromosome sites, using transposon and Cre/loxP site-specific recombination, in order to improve the conventional method requiring to prepare targeting vector and to perform PCR (polymerase chain reaction) in every experiment.

The present invention relates to a method of preparing strains deleted specific chromosome sites, using transposon and Cre/loxP site-specific recombination. More particularly the present invention relates to a method for developing novel strains deleted specific chromosome sites, by Cre/loxP site-specific recombination using transposon comprising a selectable marker and loxP site and Cre expression vector.

The method for developing novel strains deleted specific chromosome sites comprises the steps of:

(1) preparing two transposons comprising loxP site and different selectable markers;
(2) inserting the above two transposons into optional positions of microbial chromosome, respectively, and determining the inserted sites;
(3) integrating two transposons comprising different selectable markers into one chromosome by P1 phage transduction; and
(4) transforming a plasmid containing Cre gene into the host strain with the above chromosome and expressing it, to delete a chromosomal site between the two loxP sites of the transposons.

The preparation method can be explained in detail, as follows:

In the above step (1), the above two transposons have different selectable markers. In the Examples of the present invention, TnKGloxP and TnClox were prepared and used as the above two different transposons. TnKGloxP comprises loxP site (SEQ ID NO:4) and $Km^R$ (kanamycin resistant gene, SEQ ID NO:5) as a selectable marker and GFP (Green Flurolecent Protein, SEQ ID NO:6) gene. TnCloxP comprises loxP site (SEQ ID NO:4) and $Cm^R$ (chloramphenicol resistant gene, SEQ ID NO:7) as a selectable marker. The above two transposons have outer end transposase recognition sequences (OE sequence) comprising 19 base pairs at each terminus, which have SEQ ID NO:3 (5'-ctgtctcttataca-catct-3') and its reverse-complementary sequence (5'-agatgt-gtataagagacag-3'), respectively.

In other words, transposon TnKGloxP has outer end transposase recognition sequences (QE sequence) comprising 19 base pairs at each terminus, loxP site, $Km^R$ as a selectable marker and GFP gene. Transposon TnCloxP has outer end transposase recognition sequences (OE sequence) comprising 19 base pairs at each terminus, loxP site and $Cm^R$ as a selectable marker. In the above transposons, the length and the sequence of the transposon can vary depending on the vector used for the preparation of transposon except the OE sequence at each terminus and loxP site, which are essential for recombination.

Figure 1:
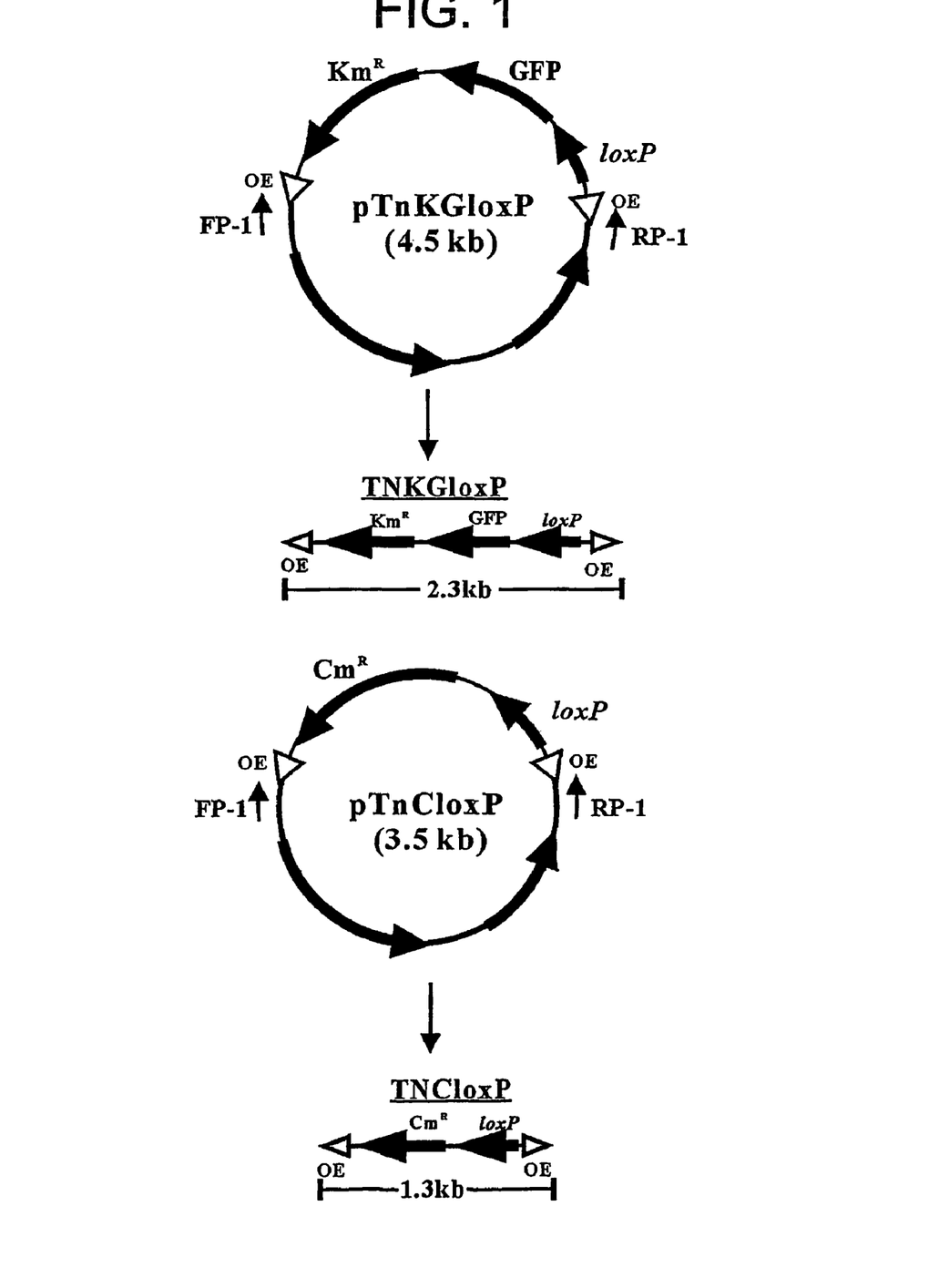
FIG. 1 shows the preparation processes and the structures of transposons TnKGloxP and TnCloxP.
Figure 2:
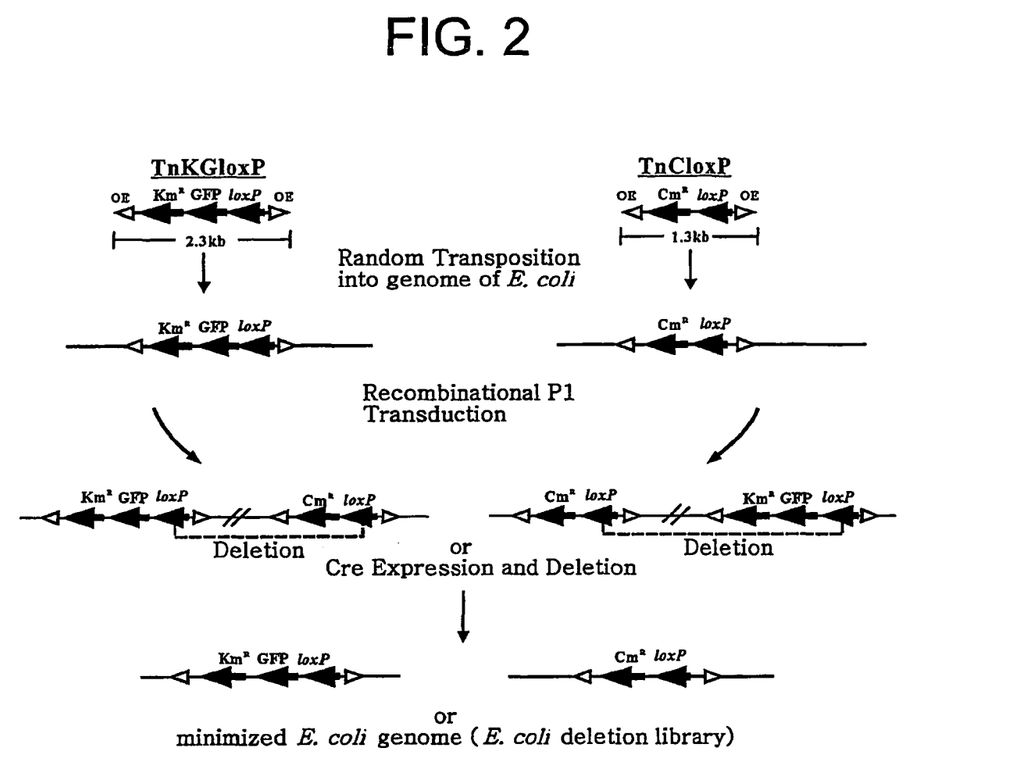
FIG. 2 shows the steps of preparing E. coli in which a specific chromosomal site is deleted by using transposons TnKGloxP and TnCloxP.

The above transposons, TnKGloxP and TnCloxP can also be obtained by PCR from the pTnKGloxP and pTnCloxP vectors, respectively (see FIG. 1).

According to one of the preferable examples, the above transposons TnKGloxP and TnCloxP may be prepared, as follow:

First, the preparation procedures of the above transposon TnKGloxP include the steps of:
  preparing a new vector pKGloxP by inserting GFP gene into pKKloxP vector comprising the linear $Km^R$ and loxP by using ligase;
  separating a DNA fragment comprising $Km^R$, GFP and loxP sites by treating pKGloxP vector with restriction enzyme;
  preparing pTnKGloxP vector by inserting the above separated DNA fragment into the linear pMODTM<MCS> vector by using ligase; and
  performing PCR of the above pTnKGloxp vector.

Also, the preparation procedures of the above transposon, TnCloxP include the steps of:
  separating a DNA fragment comprising $Cm^R$ and loxP sites by treating pKGloxP vector comprising $Cm^R$ and loxP sites with restriction enzyme;
  preparing pTnCloxP vector by inserting the above separated DNA fragment into the linear pMODTM<MCS> vector by using ligase; and
  performing PCR of the above pTnCloxP vector.

The following base sequences of the prepared Transposons TnKGloxP and TnCloxP according to the above methods, are shown as SEQ ID NO:1 and SEQ ID NO:2, respectively.

```
TnKGloxP base sequence
   1  attcaggctg cgcaactgtt gggaagggcg atcggtgcgg gcctcttcgc tattacgcca 61  gctgtctctt atacacatct caaccatcat cgatgaattc gagctcggta cccgggttga
```

|| ← OE sequence→ ||

-continued

```
 121 actgcggatc ttgcggccgc aaaaattaaa aatgaagttt tgacggtatc gaacccccaga
                        ||  ←                 Km^R
 181 gtcccgctca gaagaactcg tcaagaaggc gatagaaggc gatgcgctgc gaatcgggag
 241 cggcgatacc gtaaagcacg aggaagcggt cagcccattc gccgccaagc tcttcagcaa
 301 tatcacgggt agccaacgct atgtcctgat agcggtccgc cacacccagc cggccacagt
 361 cgatgaatcc agaaaagcgg ccattttcca ccatgatatt cggcaagcag gcatcgccat
 421 gggtcacgac gagatcctcg ccgtcgggca tccgcgcctt gagcctggcg aacagttcgg
 481 ctggcgcgag cccctgatgc tcttcgtcca gatcatcctg atcgacaaga ccggcttcca
 541 tccgagtacg tgctcgctcg atgcgatgtt tcgcttggtg gtcgaatggg caggtagccg
 601 gatcaagcgt atgcagccgc cgcattgcat cagccatgat ggatactttc tcggcaggag
 661 caaggtgaga tgacaggaga tcctgccccg gcacttcgcc caatagcagc cagtcccttc
 721 ccgcttcagt gacaacgtcg agcacagctg cgcaaggaac gcccgtcgtg gccagccacg
 781 atagccgcgc tgcctcgtct tggagttcat tcagggcacc ggacaggtcg gtcttgacaa
 841 aaagaaccgg gcgcccctgc gctgacagcc ggaacacggc ggcatgagag cagccgattg
 901 tctgttgtgc ccagtcatag ccgaatagcc tctccaccca agcggccgga gaacctgcgt
 961 gcaatccatc ttgttcaatc atgcgaaacg atcctcatcc tgtctcttga tccactagat
1021 tattgaagca tttatcaggg ttattgtctc atgagcggat acatatttga atgtatttag
1081 aaaataaac aaatagggt tccgcgcaca tttccccgaa aagtgccacc tgcatcgatg
                        Km^R                                    →  ||
1141 aattgatccg aagttcctat tctctagaaa gtataggaac ttcgaattgt cgacaagctt
1201 gatctggctt atcgaaatta atacgactca ctatagggag accggaattc attatttgta
                                                              || ← GFP
1261 gagctcatcc atgccatgtg taatcccagc agcagttaca aactcaagaa ggaccatgtg
1321 gtcacgcttt tcgttgggat ctttcgaaag ggcagattgt gtcgacaggt aatggttgtc
1381 tggtaaaagg acagggccat cgccaattgg agtattttgt tgataatggt ctgctagttg
1441 aacggatcca tcttcaatgt tgtggcgaat tttgaagtta gctttgattc cattcttttg
1501 tttgtctgcc gtgatgtata cattgtgtga gttatagttg tactcgagtt tgtgtccgag
1561 aatgtttcca tcttctttaa aatcaatacc ttttaactcg atacgattaa caagggtatc
1621 accttcaaac ttgacttcag cacgcgtctt gtagttcccg tcatctttga aagatatagt
1681 gcgttcctgt acataacctt cgggcatggc actcttgaaa aagtcatgcc gtttcatatg
1741 atccggataa cgggaaaagc attgaacacc ataagagaaa gtagtgacaa gtgttggcca
1801 tggaacaggt agttttccag tagtgcaaat aaatttaagg gtaagttttc cgtatgttgc
1861 atcaccttca ccctctccac tgacagaaaa tttgtgccca ttaacatcac catctaattc
1921 aacaagaatt gggacaactc cagtgaaaag ttcttctcct ttactcattt tttctaccgg
1981 taccccgggga tcctctagag tcgacctgca ggcatgcaag cttggcgtaa tcatggtcat
2041 agctgtttcc tgtgtgaaat tgttatccgc tcacaattcc acacaacata cgagccggaa
2101 gcataaagtg taaagcctgg ggtgcctaat gagtgagcta actcacatta attgcgttgc
2161 gctcactgcc cgctttccag tcgggaaatc caagggcgaa ttcgagctcg taccgggcc
                        GFP                       →  ||
2221 cccccctcgag *ggacctaata* *acttcgtata* *gcatacatta* *tacgaagtta* *tattaagggt*
```

```
                            -continued
                    || ←         loxP site          → ||
2281  tccggatcct ctagagtaga cctctagagt cgacctgcag gcatgcaagc ttcagggttg 2341  agatgtgtat aagagacagc tgcattaatg aatcggccaa cgcgcgggga gaggcggttt

|| ← OE sequence → ||

2401  gcgtattggg cgctcttccg cttcctcgct cactgac

TnCloxP base sequence
    1  attcaggctg cgcaactgtt gggaagggcg atcggtgcgg gcctcttcgc tattacgcca 61  gctgtctctt atacacatct caaccatcat cgatgaattc gagctcggta ccgcaaaaat

|| ← OE sequence → ||                                ||← Cm^R 121  taaaaatgaa gttttaaatc aatctaaagt atatatgagt aaacttggtc tgacagttac 181  caatgcttaa tcagtgaggc accaataact gccttaaaaa aattaegccc cgccctgcca 241  ctcatcgcag tactgttgta attcattaag cattctgccg acatggaagc catcacagac 301  ggcatgatga acctgaatcg ccagcggcat cagcaccttg tcgccttgcg tataatattt 361  gcccatggtg aaaacggggg cgaagaagtt gtccatattg gccacgttta aatcaaaact 421  ggtgaaactc acccagggat tggctgagac gaaaaacata ttctcaataa acccttaag 481  gaaataggcc aggttttcac cgtaacacgc cacatcttgc gaatatatgt gtagaaactg 541  ccggaaatcg tcgtggtatt cactccagag cgatgaaaac gtttcagttt gctcatggaa 601  aacggtgtaa caagggtgaa cactatccca tatcaccagc tcaccgtctt tcattgccat 661  acggaatttc ggatgagcat tcatcaggcg ggcaagaatg tgaataaagg ccggataaaa 721  cttgtgctta tttttcttta cggtctttaa aaaggccgta atatccagct gaacggtctg 781  gttataggta cattgagcaa ctgactgaaa tgcctcaaaa tgttctttac gatgccattg 841  ggatatatca acggtggtat atccagtgat ttttttctcc attttagctt ccttagctcc 901  tgaaaatctc gataactcaa aaaatacgcc cggtagtgat cttatttcat tatggtgaaa 961  gttggaacct cttacgtgcc gatcaacgtc tcattttcgc caaaagttgg cccagggctt 1021  cccggtatca acagggacac caggatttat ttattctgcg aagtgatctt ccgtcacagg 1081  tatttattcg gcgcaaagtg cgtcgggtga tgctgccaac ttactgattt agtgtatgat 1141  ggtgttttg aggtgctcca gtggcttctg tttctatcag catcgatgaa ttgatccgaa Cm^R →                        ||

1201  gttcctattc tctagaaagt ataggaactt cgaattgtcg acaagcttga tctggcttat 1261  cgaaattaat acgactcact atagggagac cggaattcga gctcggtacc gggcccccc 1321  tcgagggacc taataacttc gtatagcata cattatacga agttatatta agatcctcta

|| ←         loxP site          → ||

1381  gagtcgacct gcaggcatgc aagcttcagg gttgagatgt gtataagaga cagctgcatt

|| ← OE sequences → ||

1441  aatgaatcgg ccaacgcgcg gggagaggcg gtttgcgtat tgggcgctct ccgcttcct 1501  cgctcactga c
```

As mentioned above, the base sequence and the length of the remainder parts, other than loxP site, OE sequence, Km^R gene, GFP gene and Cm^R gene sites, may vary depending on the vector used for the preparation of transposon. The deletion, insertion, and/or substitution of one or more bases thereof does not change the function of transposon, if the base sequences of the loxP site, OE sequence, selectable marker (Km^R/GFP or Cm^R) are all included and preserved. Further, loxP site is located between the outer end transposase recognition sequences on both termini, and not inserted in the middle or the inside of the selectable marker, wherein it does not matter that loxP site is located in 3' side or 5' side of the selectable marker.

In the above step (2), transposases are added to the above two transposons TnKGloxP and TnCloxP, respectively, to form transposome, respectively; the transposomes including different transposons are transferred to different microorganisms using electrophoration; each transposon is inserted into the random site of the chromosomes of the microorganism; mutant microorganism inserted with the above transposon is selected; and the insertion site of the transposon in the selected mutants is identified. Since the random inserting function of the transposase can be activated by $Mg^{2+}$ ion, the formation of transposome is carried out in the absence of $Mg^{2+}$ ion, and the random insertion of transposon in the microorganism is carried out in the presence of $Mg^{2+}$ ion.

Also, since the two transposons include kanamycin resistant gene and chloramphenicol resistant gene, respectively, and thus, they are resistant against the above two antibiotics, the strains with the respective transposon can be selected by cultivating them in the kanamycin- or chloramphenicol-containing media after inserting the above transposon thereto. The random insertion of transposon can be identified by Southern blot analysis, and the position of the inserted transposon can be confirmed by arbitrary PCR.

In the above step (3), a strain inserted with one transposon at one of the termini of the chromosomal site to be deleted and a strain inserted with other kind of transposon are collected from the strains in which the position of transposon have been identified. Using one of the selected strains as the donor and the other as recipient, the above two transposons are located on both ends of the chromosomal site to be deleted by general P1 phage transduction method, wherein the loxP sites must be located in the same direction.

In the above step (4), Cre gene is transferred into the mutant strain containing transposons on both ends of the chromosomal site to be deleted by transferring the pTSCre expression vector into the above mutant strain. Since the transcription of the Cre gene in the pTSCre expression vector is controlled by tetracycline promoter (Ptet), Cre Recombinase is synthesize by expressing Cre gene by cultivating the mutant strain introduced with the above pTSCre expression vector in the medium containing chlorotetracycline. Cre Recombinase in this synthesis helps to remove the chromosomal site containing two loxP sites in either end by specifically cleaving the above two loxP sites and ligating the cleavage sites.

In addition, the preparation methods according to the present invention can additionally include the step of repeatedly performing steps (3) and (4) on the mutant strains containing deletions of a partial chromosomal site to reduce the size of the chromosome by degrees. In other words, by randomly selecting two from the mutants containing deletions of the above specific chromosomal sites; fusing the chromosoms of the two selected mutants into one chromosome by P1 phage transduction to obtaining a new strain containing an extended chromosomal deletion site as large as the deleted sites of the above two mutants' chromosomes; and further extending the deleted site of the chromosome by continuously performing P1 phage transduction between the obtained new strain repeatedly and another mutant to reduce the size of the chromosome of mutant by degrees, a mutant with a larger deleted site of chromosome is obtained. In the continuous P1 phage transduction, in order to efficiently select the mutant with the desired deletion site, selectable marker acting as P1 recipient is removed by homologous recombination.

In the present invention, E. coli was used as the above microorganism, and Tn5 was used as the above transposon. It has been reported that Tn5 can be inserted into an random site of the chromosome (Berg, D. D., and M. M. Howe. 1989. Mobile DNA. American Society for Microbiology, Washington, D.C.), and Cre DNA recombinase recognizes the two loxP sites to catalyze the DNA recombination reaction between them (Abremski, K., HoessR., and Sternberg, N. 1984. Studies on the properties of P1 site-specific recombination. Cell 32, 1301-1311).

Also, P1 phage is known to have a function transferring a part of the chromosome of the host microorganism to other microorganism (Watanabe, T, Furuse, C., and Sakaizumi, S. 1968. Transduction of various R factors by phage P1 in Escherichia coli and by phage P22 in Salmonella typhimurium). Therefore, the present invention develops a method of novel mutant microorganism containing deletion of a partial chromosomal site between two loxP sites, by inserting the transposon with loxP site into an random site of the microorganism chromosome, positioning two loxP sites inside a single chromosome in the same direction by using P1 phage transformation, and introducing Cre expressing vector to express Cre DNA Recombinase.

The invention will be further illustrated by the following examples. It will be apparent to those having conventional knowledge in the field that these examples are given only to explain the present invention more clearly, but the invention is not limited to the examples given.

EXAMPLE 1

Preparation of Transposons TnKGloxP and TnCloxP that can be Inserted into Random Site in the E. coli Chromosome FIG. 1 represents a linear transposons TnKGloxP and TnCloxP, wherein TnKGloxP contains $Km^R$, GFP (pGFPuv, Clontech, Palo Alto, Calif.) and loxP, and TnCloxP contains $Cm^R$ and loxP sites. The above two transposons have outer end transposase recognition sequences (O Epicentre technologies, Madison, Wis.) comprising 19 base pairs at each terminus. As can be seen in FIG. 1, the above transposons TnKGloxP and TnCloxP can be obtained by PCR from pTnKGloxP and pTnCloxP vectors, respectively.

The above pTnKGloxP vector was prepared by the following method. First, after GFP gene obtained from PCR was cleaved by EcoRI restriction enzyme (New England Biolabs, Beverly, Mass.), the GFP gene was inserted into vector pKK-loxP (Michael D. Koob, et al, 1994, In vivo excision and amplification of large segment of the Escherichia coli genome, Nucleic Acids Research 22(12), 2392-2398) which was cleaved by EcoRI restriction enzyme to be a linear form and with $Km^R$ and loxP sites, by using ligase (New England Biolabs, Beverly, Mass.), to obtain a novel vector. The novel vector was named as pKGloxP.

After separating the DNA fragment of 2.2 kb having $Km^R$ gene, GFP gene and loxP site by reacting the above pKGloxP with NotI/XbaI restriction enzyme (New England Biolabs, Beverly, Mass.), the separated DNA fragment was inserted by using ligase into linear pMODTM<MCS> (Epicentre technologies, Madison, Wis.) treated with BamHI restriction enzyme, to obtain vector pTnKGloxP (see FIG. 1).

The above pTnCloxP vector was prepared as follows: After separating 1.2 kb sized DNA fragment having $Cm^R$ and loxP sites by cleaving pKCloxP (Michael D. Koob, et al, 1994, In vivo excision and amplification of large segment of the *Escherichia coli* genome, Nucleic Acids Research 22(12), 2392-2398) vector containing $Cm^R$ and loxP sites with NotI and BamHI restriction enzymes (New England Biolabs, Beverly, Mass.), the above DNA fragment was inserted by using ligase into linear pMODTM<MCS> vector treated with BamHI restriction enzyme to prepare pTnCloxP vector (FIG. 1).

Transposon TnKGloxP and TnCloxP were prepared from the above pTnKGloxP and pTnCloxP vectors, respectively by PCR. The primers used in the above PCR are pMOD<MCS>FP-1 (SEQ ID NO:8) and pMOD<MCS>RP-1 (SEQ ID NO:9) with the following base sequence.

```
pMOD<MCS>FP-1    5'-ATTCAGGCTGCGCAACTGT-3' pMOD<MCS>RP-1    5'-TCAGTGAGCGAGGAAGCGGAAG-3'
```

EXAMPLE 2

Preparation of Two Kinds of *E. coli* Mutant Libraries Inserted with Transposons TnKGloxP and TnCloxP into Ranom Sites of *E. coli* Chromosome and Identification of the Insertion Site After reacting 500 ng of TnKGloxP and 500 ng of TnCloxP with 10 μl of Tn5 transposase, respectively, and adding DDW (Double Distilled Water) to make the total volume of the solution to 20 μl, each transposome was formed by reacting at 25° C. for 30 min. To inhibit the random insertion function of the transposase, the above reaction was carried out in the absence of $Mg^{2+}$ ion. One microliter of the transposome was transferred into *E. coli* strain MG1655 (Seoul National University Biological Sceince Division, Dr. J. H. Noh) by conventional electrophoration method [Bio-RAD, Bacterial electro-transformation and Plus Controller Instruction Manual, Cat. No 165-2098; Thompson, J R, et al. An improved protocol for the preparation of yeast cells for transformation by electrophoration. Yeast 14, 565-571 (1998); Grant, S G, et al. Differential plasmid rescue from transgenic mouse DNAs into *Escherichia coli* methyllation-restriction mutants. Proc. Natl. Acad. Sci. USA 87, 4645-4649 (1990)], in the presence of $Mg^{2+}$ ion. LB medium (tryptone 1%, yeast extract 0.5%, NaCl 0.5%) was used for the cultivation of the strain, wherein a small amount of $Mg^{2+}$ ion was contained.

Therefore, the random insertion function of transposase can be activated by $Mg^{2+}$ ion inside *E. coli* cells, and transposome can be inserted into the *E. coli* chromosome at random sites. Since the *E. coli* mutant comprising the above two transposons inserted have kanamycin or chloramphenicol resistance due to $Km^R$ or $Cm^R$ gene in the transposons, they were selected in the kanamycin or chloramphenicol media. Each transposon inserted into the chromosome of *E. coli* MG1655 was identified by Southern blot analysis.

The conditions for Southern blot analysis were as follows: After separating the chromosomal DNA from the *E. coli* mutant in which transposon was inserted and cleaving the chromosomal DNA by using ClaI restriction enzyme (New England Biolabs, Beverly, Mass.), electrophoresis was performed on 1% agarose gel. DNA in the agarose gel was transferred onto HYBOND N+ membrane (Amersham) and the transferred DNA was blotted by using $^{32}P$-labled $Km^R$ or $Cm^R$ gene as probe. The transposon insertion site was confirmed by arbitrary PCR (Caetano-Annoles, G. 1993. Amplifying DNA with arbitrary oligonucleotide primers. PCR Methods Appl., 3, 85-92).

DNA around the transposon insertion site was amplified using Tn5 insertion sequence specific primer and the primer that can arbitrarily bind to the chromosomal DNA at the outer side of transposon. The above arbitrary PCR was composed of two steps:

In the first step, single strand DNA containing the end sequence of transposon and the outer sequence thereof by using transposon specific primer Tn5Ext (5'-AGCATACAT-TATACGAAGTTATATTAAG-3' (SEQ ID NO: 10), synthesized by Genotech), and subsequently, the primer Arbi (5'-TTGAGCGATAGACGTACGAINNNNNNNNNNGATAT-3' (SEQ ID NO: 11)), synthesized by Genotech) binding to nonspecific site was bound to an nonspecific site of the above synthesized single strand DNA, to synthesize double strand DNA.

Figure 3A:
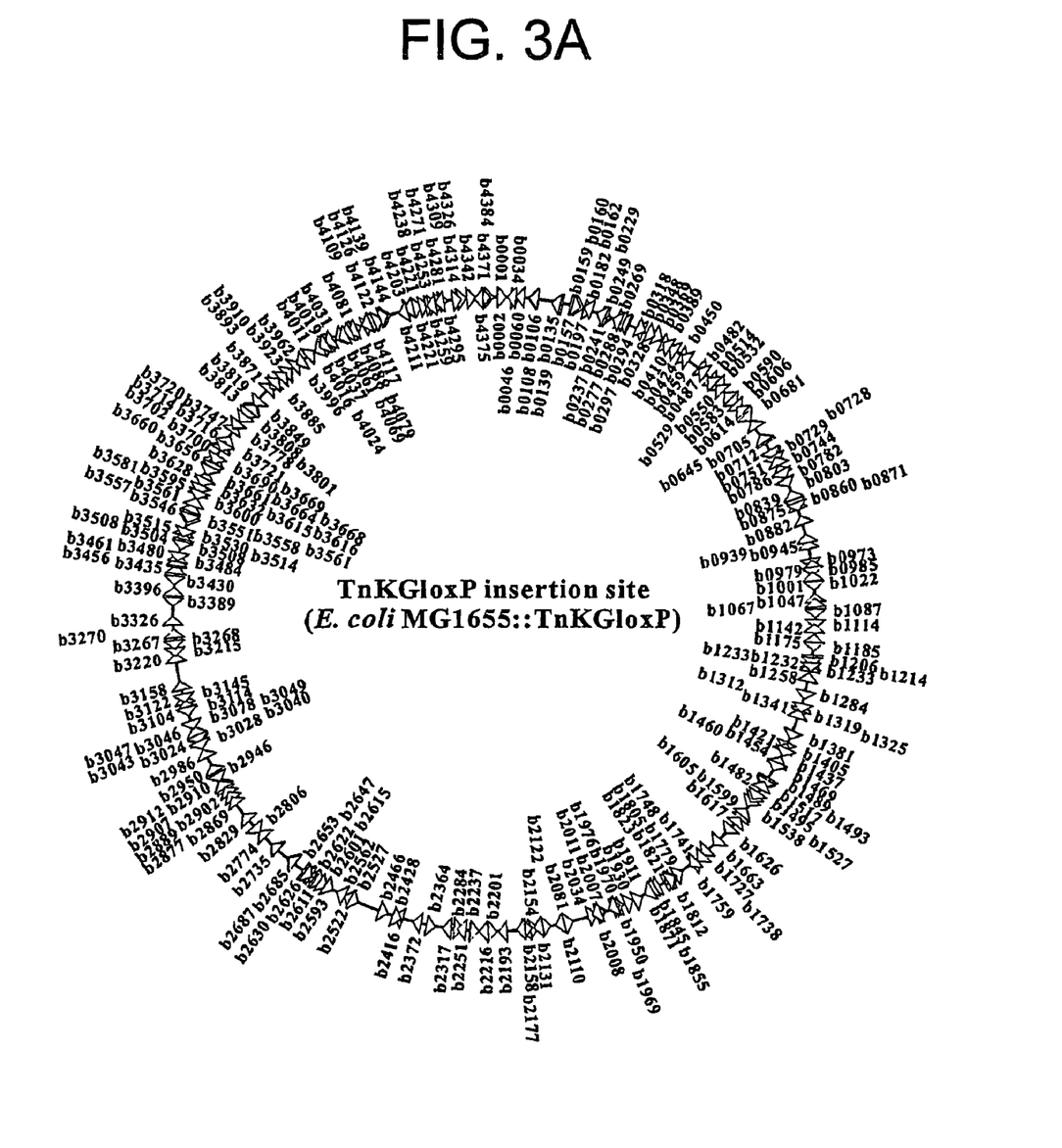
FIGS. 3A and 3B show the sites that can be inserted with TnKGloxP and TnCloxP in the E. coli genome.
Figure 3B:
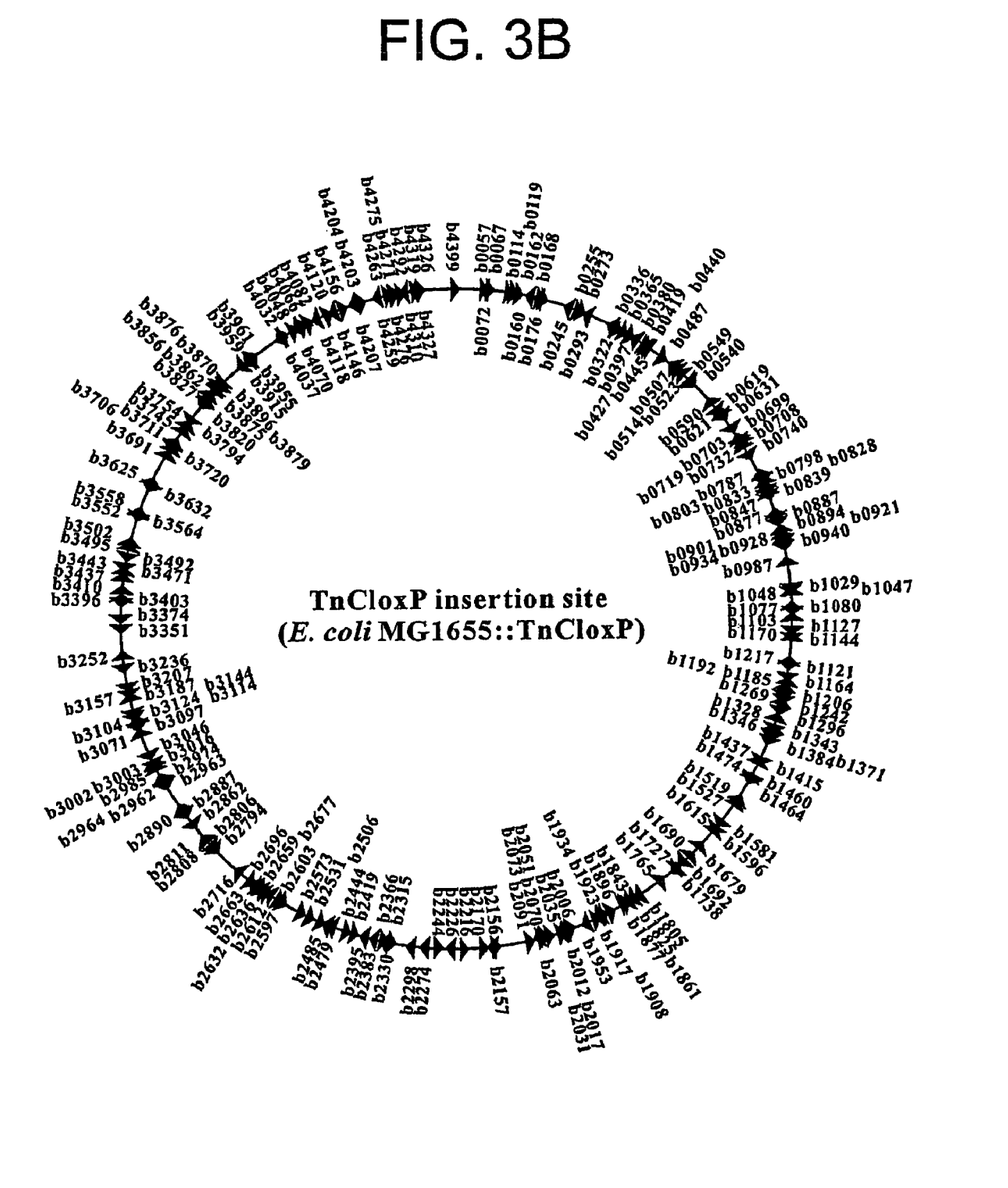

In the second step, the above synthesized double strand DNA was amplified in large scale by using transposon specific primer Tn5Int and primer Arb2 (5'-TTGAGCGATA-GACGTACGAT-3' (SEQ ID NO: 12), synthesized by Genotech) whose base sequence is identical to 25 sequence of 3' end of Arb1. The amplified DNA was separated from the agarose gel by using QIAQUICK spin PCR purification kit (Qiagen), the base sequence of the above separated DNA was analyzed using primer In5Int (5' TCGACCTGCAGGCATG-CAAGCTTCA-3' (SEQ ID NO: 13), synthesized by Genotech), and the insertion site was identified by comparing the above analysis result with GENBANK DNA sequence by using BLAST program. The identified insertion sites of TnK-GloxP and TnCloxP by the above methods are shown in FIG. 3.

EXAMPLE 3

Construction of *E. coil* Mutant Containing Two Transposons on the Chromosome by P1 Phage Transduction Two mutants with the two different transposons at one end and the other end of the specific chromosomal site to be removed, respectively, were selected from the TnKGloxP mutant library and TnCloxP mutant library prepared according to Example 2. Then, the two chromosomes with the different transposons were integrated in a single chromosome by P1 phage transduction so that one transposons should be located on one end of the chromosomal site to be removed and the other transposon should be located on the other end. The loxP was positioned in the same direction, and P1 phage transduction was carried out by following a well-known protocol (Miller, J., H., editors, 1992, A short Course in Bacterial Genetics; A Laboratory Manual and Handbook for *Escherichia coli* and Related Bacteria, New York: Cold Spring Harbor).

EXAMPLE 4

Construction of *E. coli* Mutant Containing Deletion Mutation by Expressing Cre DNA Recombinase by Transferring pTSCre Expression Vector pTSCre expression vector (Yoon Y G, et al, 1998, Cre/loxP-mediated excision and amplification of the *Eshcerichia coli* genome, Gene 14, 89-95) was transferred into the *E. coli* mutant with TnKGloxP and TnCloxP on either end of the chromosomal site to be deleted. Since the transcription of the Cre gene existing in the pTSCre expression vector is controlled by tetracycline promoter (Ptet), the mutant was cultivated in the medium containing chlorotetracycline at 42° C., to express Cre recombinase. E. coli mutant with chromosome deletion mutation obtained from the result of expression of Cre DNA recombinase was confirmed by PCR.

Figure 4A:
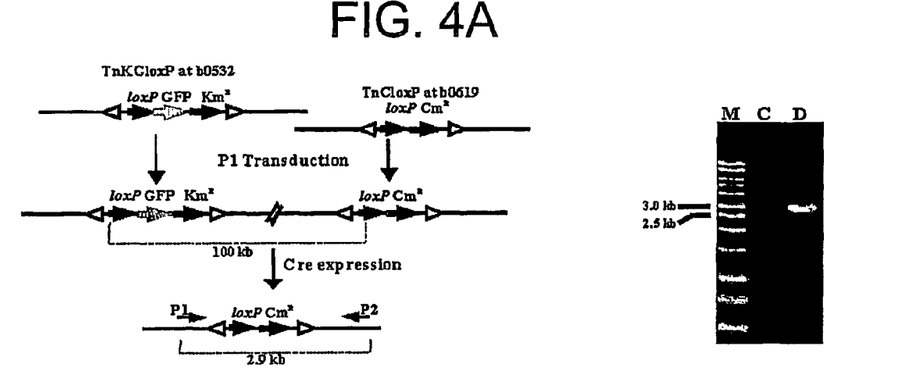
FIG. 4A through 4D show the method of deleting specific sites of E. coli chromosome by using transposons TnKGloxP and TnCloxP inserted in various sites and the PCR results of the deleted chromosome.
Figure 4B:
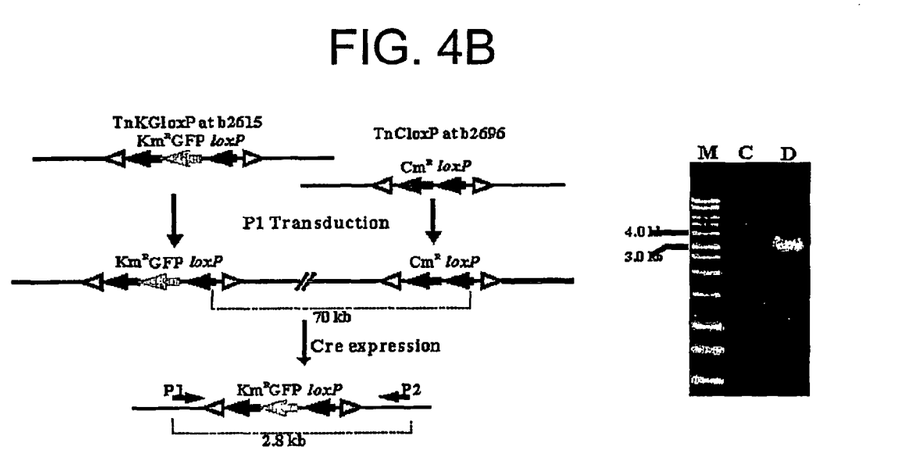
Figure 4C:
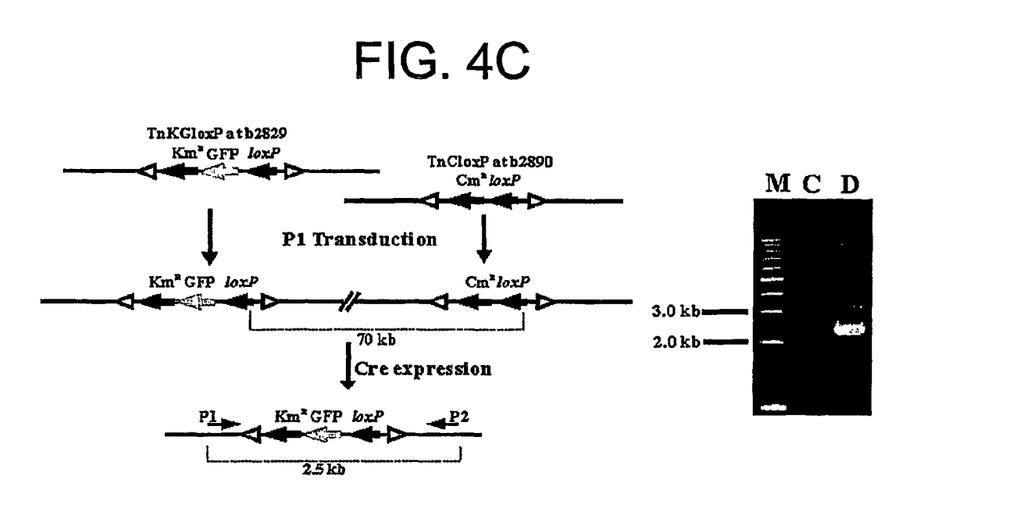
Figure 4D:
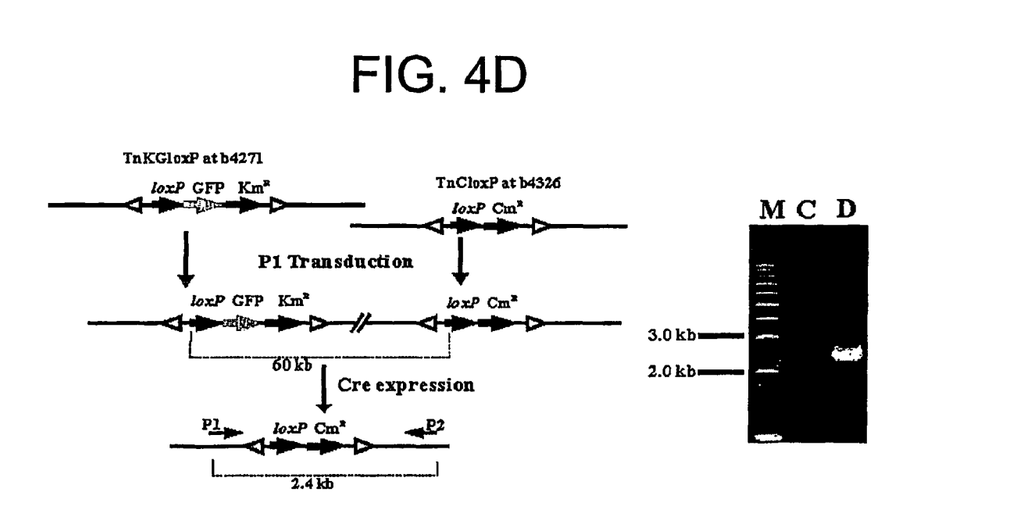

In the Examples 3 and 4, a mutant in which TnKGloxP was inserted at b0532 site and a mutant in which TnCloxP was inserted at b0619 site; a mutant in which TnKGloxP was inserted at b2011 site and a mutant in which TnCloxP was inserted at b2073 site; a mutant in which TnKGloxP was inserted b2829 site and a mutant in which TnCloxP was inserted at b2890 site; and a mutant in which TnKGloxP was inserted at b4271 site and a mutant in which TnCloxP was inserted at b4326 site were used for P1 transduction to express Cre gene. The results are shown in FIGS. 4A, B. C and D.

EXAMPLE 5

Construction of Mutant with Extended Chromosomal Deletion Site by Repeatedly Performing P1 Phage Transduction Method The chromosomal deletion site of E. coli mutant containing a specific chromosomal sites were deleted was extended by P1 phage transduction as mentioned in the above Example 3 and 4. First, two mutants were selected from the above specific chromosome site deleted mutants. Using one of them as the donor, and the other as recipient of P1 phage lysate, a new mutant was prepared, in which all of the chromosomal deletion sites of the above two mutants were deleted. Then, this mutant was used again as P1 phage recipient, and the already prepare mutant containing other chromosomal deletion site was used as donor to perform P1 phage transduction continuously and repeatedly. By this method, a chromosomal deletion site of other mutant was repeatedly removed from the chromosome of the above obtained mutant. In the continuous P1 phage transduction, in order to efficiently select the microorganism, selectable marker that acts as P1 recipient was eliminated by homologous recombination.

INDUSTRIAL APPLICABILITY

As mentioned above, the present invention related to a method of developing novel E. coil strain deleted specific chromosome sites, using transposon and Cre/loxP site-specific recombination. Various sites of E. coli chromosome can be selectively and efficiently removed, and library of E. coli mutants containing deletions of specific chromosomal sites can be obtained, and a variety of E. coli mutants with selectively reduced chromosome can be created by repeatedly performing P1 phage transformation and reducing the chromosome by degrees. By the method of the present invention, nonessential gene for the growth of E. coil can be removed, and genetically simplified E. coli mutant can be constructed that can be used for the functional research in genomics. Also, fast growing E. coil mutant can be selected and used as artificial cell line, since nonessential genes for growth were eliminated. Also, the present invention can be applied to other microorganisms other than E. coli, and therefore a variety of mutant microorganisms can be created with selectively reduced chromosomes. Also, in the minimized chromosome prepared according to the method of the present invention, a cassette made by collecting foreign genes related to new metabolism can be constructed and introduced in organisms, to create novel organisms having a variety of useful functions

The invention claimed is:

1. A transposon comprising the outer end transposase recognition sequence of SEQ ID NO: 3 on one end of the transposon, the reverse-complementary sequence of SEQ ID NO: 3 on the other end of the transposon, the loxP sequence of SEQ ID NO: 4, the kanamycin resistance ($Km^R$) sequence of SEQ ID NO: 5 and green fluorescent protein (GFP) sequence of SEQ ID NO: 6.

2. The transposon according to claim 1, comprising the sequence of SEQ ID NO: 1.

3. A transposon comprising the sequence of SEQ ID NO: 2.

4. A method for constructing novel strains containing deletion of a specific chromosomal site, characterized in comprising the steps of:
   (a) preparing a first transposon according to claim 1 and a second transposon comprising the sequence of SEQ ID NO: 2,
   (b) inserting said first and second transposons, respectively, into random positions of different microbial chromosomes and determining the inserted sites;
   (c) integrating the two microbial chromosomes by P1 phage transduction to position the first and second transposons on one chromosome; and
   (d) deleting a chromosomal site between the two loxP sites by expressing Cre gene from a Cre expression vector.

5. A method for constructing novel strains containing deletion of a specific chromosomal site, characterized in comprising the steps of:
   (a) preparing a first transposon according to claim 2 and a second transposon comprising the sequence of SEQ ID NO: 2,
   (b) inserting said first and second transposons, respectively, into random positions of different microbial chromosomes and determining the inserted sites;
   (c) integrating the two microbial chromosomes by P1 phage transduction to position the first and second transposons on one chromosome; and
   (d) deleting a chromosomal site between the two loxP sites by expressing Cre gene from a Cre expression vector.

6. The method for constructing novel strains according to claim 4 or claim 5, additionally comprising the steps of:
   selecting two mutants from the mutants containing deletion of a specific chromosomal site, and performing P1 phage transduction using one of the selected mutants as the donor and the other as recipient, to construct a new mutant containing all chromosomal deletion sites of the above two mutants; and
   using the above obtained mutant again as P1 phage recipient, and the already prepared mutant containing deletion of a specific chromosomal site as donor to perform P1 phage transduction continuously and repeatedly to reduce the chromosome of the obtained mutant by degrees.

* * * * *

SEQUENCE LISTING

```
<160> NUMBER OF SEQ ID NOS: 13

<210> SEQ ID NO 1
<211> LENGTH: 2437
<212> TYPE: DNA
<213> ORGANISM: Artificial Sequence
<220> FEATURE:
<223> OTHER INFORMATION: TnKGloxP

<400> SEQUENCE: 1
attcaggctg cgcaactgtt gggaagggcg atcggtgcgg gcctcttcgc tattacgcca      60
gctgtctctt atacacatct caaccatcat cgatgaattc gagctcggta cccgggttga     120
actgcggatc ttgcggccgc aaaaattaaa aatgaagttt tgacggtatc gaacccaga     180 gtcccgctca gaagaactcg tcaagaaggc gatagaaggc gatgcgctgc gaatcgggag     240
cggcgatacc gtaaagcacg aggaagcggt cagcccattc gccgccaagc tcttcagcaa     300
tatcacgggt agccaacgct atgtcctgat agcggtccgc cacacccagc cggccacagt     360
cgatgaatcc agaaaagcgg ccattttcca ccatgatatt cggcaagcag gcatcgccat     420
gggtcacgac gagatcctcg ccgtcgggca tccgcgcctt gagcctggcg aacagttcgg     480
ctggcgcgag cccctgatgc tcttcgtcca gatcatcctg atcgacaaga ccggcttcca     540
tccgagtacg tgctcgctcg atgcgatgtt tcgcttggtg gtcgaatggg caggtagccg     600
gatcaagcgt atgcagccgc cgcattgcat cagccatgat ggatactttc tcggcaggag     660
```

-continued

| | |
|---|---|
| caaggtgaga tgacaggaga tcctgccccg gcacttcgcc caatagcagc cagtcccttc | 720 |
| ccgcttcagt gacaacgtcg agcacagctg cgcaaggaac gcccgtcgtg gccagccacg | 780 |
| atagccgcgc tgcctcgtct tggagttcat tcagggcacc ggacaggtcg gtcttgacaa | 840 |
| aaagaaccgg gcgcccctgc gctgacagcc ggaacacggc ggcatcagag cagccgattg | 900 |
| tctgttgtgc ccagtcatag ccgaatagcc tctccaccca agcggccgga gaacctgcgt | 960 |
| gcaatccatc ttgttcaatc atgcgaaacg atcctcatcc tgtctcttga tccactagat | 1020 |
| tattgaagca tttatcaggg ttattgtctc atgagcggat acatatttga atgtatttag | 1080 |
| aaaaataaac aaatagggt tccgcgcaca tttccccgaa aagtgccacc tgcatcgatg | 1140 |
| aattgatccg aagttcctat tctctagaaa gtataggaac ttcgaattgt cgacaagctt | 1200 |
| gatctggctt atcgaaatta atacgactca ctataggga accggaattc attatttgta | 1260 |
| gagctcatcc atgccatgtg taatcccagc agcagttaca aactcaagaa ggaccatgtg | 1320 |
| gtcacgcttt tcgttgggat cttcgaaag gcagattgt gtcgacaggt aatggttgtc | 1380 |
| tggtaaaagg acagggccat cgccaattgg agtattttgt tgataatggt ctgctagttg | 1440 |
| aacggatcca tcttcaatgt tgtggcgaat tttgaagtta gctttgattc cattcttttg | 1500 |
| tttgtctgcc gtgatgtata cattgtgtga gttatagttg tactcgagtt tgtgtccgag | 1560 |
| aatgtttcca tcttctttaa aatcaatacc ttttaactcg atacgattaa caagggtatc | 1620 |
| accttcaaac ttgacttcag cacgcgtctt gtagttcccg tcatctttga agatatagt | 1680 |
| gcgttcctgt acataacctt cgggcatggc actcttgaaa aagtcatgcc gtttcatatg | 1740 |
| atccggataa cgggaaaagc attgaacacc ataagagaaa gtagtgacaa gtgttggcca | 1800 |
| tggaacaggt agtttttccag tagtgcaaat aaatttaagg gtaagttttc cgtatgttgc | 1860 |
| atcaccttca ccctctccac tgacagaaaa tttgtgccca ttaacatcac catctaattc | 1920 |
| aacaagaatt gggacaactc cagtgaaaag ttcttctcct ttactcattt tttctaccgg | 1980 |
| tacccgggga tcctctagag tcgacctgca ggcatgcaag cttggcgtaa tcatggtcat | 2040 |
| agctgtttcc tgtgtgaaat tgttatccgc tcacaattcc acacaacata cgagccggaa | 2100 |
| gcataaagtg taaagcctgg ggtgcctaat gagtgagcta actcacatta attgcgttgc | 2160 |
| gctcactgcc cgcttttccag tcgggaaatc caagggcgaa ttcgagctcg gtaccgggcc | 2220 |
| ccccctcgag ggacctaata acttcgtata gcatacatta tacgaagtta tattaagggt | 2280 |
| tccggatcct ctagagtaga cctctagagt cgacctgcag gcatgcaagc ttcagggttg | 2340 |
| agatgtgtat aagagacagc tgcattaatg aatcggccaa cgcgcgggga gaggcggttt | 2400 |
| gcgtattggg cgctcttccg cttcctcgct cactgac | 2437 |

<210> SEQ ID NO 2
<211> LENGTH: 1511
<212> TYPE: DNA
<213> ORGANISM: Artificial Sequence
<220> FEATURE:
<223> OTHER INFORMATION: TnCloxP

<400> SEQUENCE: 2

| | |
|---|---|
| attcaggctg cgcaactgtt gggaagggcg atcggtgcgg gcctcttcgc tattacgcca | 60 |
| gctgtctctt atacacatct caaccatcat cgatgaattc gagctcggta ccgcaaaaat | 120 |
| taaaaatgaa gttttaaatc aatctaaagt atatatgagt aaacttggtc tgacagttac | 180 |
| caatgcttaa tcagtgaggc accaataact gccttaaaaa aattacgccc cgccctgcca | 240 |
| ctcatcgcag tactgttgta attcattaag cattctgccg acatggaagc catcacagac | 300 |

```
ggcatgatga acctgaatcg ccagcggcat cagcaccttg tcgccttgcg tataatattt      360
gcccatggtg aaaacggggg cgaagaagtt gtccatattg gccacgttta aatcaaaact      420
ggtgaaactc acccagggat tggctgagac gaaaaacata ttctcaataa acccttagg       480 gaaataggcc aggttttcac cgtaacacgc cacatcttgc gaatatatgt gtagaaactg      540
ccggaaatcg tcgtggtatt cactccagag cgatgaaaac gtttcagttt gctcatggaa      600
aacggtgtaa caagggtgaa cactatccca tatcaccagc tcaccgtctt tcattgccat      660
acggaatttc ggatgagcat tcatcaggcg ggcaagaatg tgaataaagg ccggataaaa      720
cttgtgctta ttttctttta cggtctttaa aaaggccgta atatccagct gaacggtctg      780
gttataggta cattgagcaa ctgactgaaa tgcctcaaaa tgttctttac gatgccattg      840
ggatatatca acggtggtat atccagtgat ttttttctcc attttagctt ccttagctcc      900
tgaaaatctc gataactcaa aaaatacgcc cggtagtgat cttatttcat tatggtgaaa      960
gttggaacct cttacgtgcc gatcaacgtc tcattttcgc caaagttggc ccagggctt       1020 cccggtatca cagggacac caggatttat ttattctgcg aagtgatctt ccgtcacagg       1080
tatttattcg gcgcaaagtg cgtcgggtga tgctgccaac ttactgattt agtgtatgat      1140 ggtgttttg aggtgctcca gtggcttctg tttctatcag catcgatgaa ttgatccgaa       1200
gttcctattc tctagaaagt ataggaactt cgaattgtcg acaagcttga tctggcttat      1260
cgaaattaat acgactcact atagggagac cggaattcga gctcggtacc gggccccccc      1320
tcgagggacc taataacttc gtatagcata cattatacga agttatatta agatcctcta      1380
gagtcgacct gcaggcatgc aagcttcagg gttgagatgt gtataagaga cagctgcatt      1440
aatgaatcgg ccaacgcgcg gggagaggcg gtttgcgtat tgggcgctct tccgcttcct      1500
cgctcactga c                                                           1511
```

<210> SEQ ID NO 3
<211> LENGTH: 19
<212> TYPE: DNA
<213> ORGANISM: Artificial Sequence
<220> FEATURE:
<223> OTHER INFORMATION: Outer end transposon recognition (OE) sequence

<400> SEQUENCE: 3

```
ctgtctctta tacacatct                                                   19
```

<210> SEQ ID NO 4
<211> LENGTH: 34
<212> TYPE: DNA
<213> ORGANISM: Artificial Sequence
<220> FEATURE:
<223> OTHER INFORMATION: loxP site

<400> SEQUENCE: 4

```
ataacttcgt atagcataca ttatacgaag ttat                                  34
```

<210> SEQ ID NO 5
<211> LENGTH: 996
<212> TYPE: DNA
<213> ORGANISM: Artificial Sequence
<220> FEATURE:
<223> OTHER INFORMATION: KmR gene

<400> SEQUENCE: 5

```
gcaaaaatta aaaatgaagt tttgacggta tcgaacccca gagtcccgct cagaagaact      60
```

-continued

```
cgtcaagaag gcgatagaag gcgatgcgct gcgaatcggg agcggcgata ccgtaaagca      120
cgaggaagcg gtcagcccat tcgccgccaa gctcttcagc aatatcacgg gtagccaacg      180
ctatgtcctg atagcggtcc gccacaccca gccggccaca gtcgatgaat ccagaaaagc      240
ggccattttc caccatgata ttcggcaagc aggcatcgcc atgggtcacg acgagatcct      300
cgccgtcggg catccgcgcc ttgagcctgg cgaacagttc ggctggcgcg agcccctgat      360
gctcttcgtc cagatcatcc tgatcgacaa gaccggcttc catccgagta cgtgctcgct      420
cgatgcgatg tttcgcttgg tggtcgaatg ggcaggtagc cggatcaagc gtatgcagcc      480
gccgcattgc atcagccatg atggatactt tctcggcagg agcaaggtga gatgacagga      540
gatcctgccc cggcacttcg cccaatagca gccagtccct ccccgcttca gtgacaacgt      600
cgagcacagc tgcgcaagga acgcccgtcg tggccagcca cgatagccgc gctgcctcgt      660
cttggagttc attcagggca ccggacaggt cggtcttgac aaaaagaacc gggcgcccct      720
gcgctgacag ccggaacacg gcggcatcag agcagccgat tgtctgttgt gcccagtcat      780
agccgaatag cctctccacc caagcggccg gagaacctgc gtgcaatcca tcttgttcaa      840
tcatgcgaaa cgatcctcat cctgtctctt gatccactag attattgaag catttatcag      900
ggttattgtc tcatgagcgg atacatattt gaatgtattt agaaaaataa acaaataggg      960
gttccgcgca catttccccg aaaagtgcca cctgca                               996
```

```
<210> SEQ ID NO 6
<211> LENGTH: 947
<212> TYPE: DNA
<213> ORGANISM: Artificial Sequence
<220> FEATURE:
<223> OTHER INFORMATION: GFP gene

<400> SEQUENCE: 6
```

```
attatttgta gagctcatcc atgccatgtg taatcccagc agcagttaca aactcaagaa       60
ggaccatgtg gtcacgcttt tcgttgggat ctttcgaaag ggcagattgt gtcgacaggt      120
aatggttgtc tggtaaaagg acagggccat cgccaattgg agtattttgt tgataatggt      180
ctgctagttg aacggatcca tcttcaatgt tgtggcgaat tttgaagtta gctttgattc      240
cattcttttg tttgtctgcc gtgatgtata cattgtgtga gttatagttg tactcgagtt      300
tgtgtccgag aatgtttcca tcttctttaa aatcaatacc ttttaactcg atacgattaa      360
caagggtatc accttcaaac ttgacttcag cacgcgtctt gtagttcccg tcatctttga      420
aagatatagt gcgttcctgt acataacctt cgggcatggc actcttgaaa aagtcatgcc      480
gtttcatatg atccggataa cgggaaaagc attgaacacc ataagagaaa gtagtgacaa      540
gtgttggcca tggaacaggt agttttccag tagtgcaaat aaatttaagg gtaagttttc      600
cgtatgttgc atcaccttca ccctctccac tgacagaaaa tttgtgccca ttaacatcac      660
catctaattc aacaagaatt gggacaactc cagtgaaaag ttcttctcct ttactcattt      720
tttctaccgg tacccgggga tcctctagag tcgacctgca ggcatgcaag cttggcgtaa      780
tcatggtcat agctgtttcc tgtgtgaaat tgttatccgc tcacaattcc acacaacata      840
cgagccggaa gcataaagtg taaagcctgg ggtgcctaat gagtgagcta actcacatta      900
attgcgttgc gctcactgcc cgctttccag tcgggaaatc caagggc                   947
```

```
<210> SEQ ID NO 7
<211> LENGTH: 1069
<212> TYPE: DNA
<213> ORGANISM: Artificial Sequence
```

<220> FEATURE:
<223> OTHER INFORMATION: CmR gene

<400> SEQUENCE: 7

```
gcaaaaatta aaaatgaagt tttaaatcaa tctaaagtat atatgagtaa acttggtctg      60
acagttacca atgcttaatc agtgaggcac caataactgc cttaaaaaaa ttacgccccg     120
ccctgccact catcgcagta ctgttgtaat tcattaagca ttctgccgac atggaagcca    180
tcacagacgg catgatgaac ctgaatcgcc agcggcatca gcaccttgtc gccttgcgta    240
taatatttgc ccatggtgaa aacggggggcg aagaagttgt ccatattggc cacgtttaaa    300
tcaaaactgg tgaaactcac ccagggattg gctgagacga aaaacatatt ctcaataaac    360
cctttaggga ataggccag gttttcaccg taacacgcca catcttgcga atatatgtgt      420
agaaactgcc ggaaatcgtc gtggtattca ctccagagcg atgaaaacgt ttcagtttgc    480
tcatggaaaa cggtgtaaca agggtgaaca ctatcccata tcaccagctc accgtctttc    540
attgccatac ggaatttcgg atgagcattc atcaggcggg caagaatgtg aataaaggcc    600
ggataaaact tgtgcttatt tttctttacg gtctttaaaa aggccgtaat atccagctga    660
acggtctggt tataggtaca ttgagcaact gactgaaatg cctcaaaatg ttctttacga    720
tgccattggg atatatcaac ggtggtatat ccagtgattt ttttctccat tttagcttcc    780
ttagctcctg aaaatctcga taactcaaaa aatacgcccg gtagtgatct tatttcatta    840
tggtgaaagt tggaacctct tacgtgccga tcaacgtctc attttcgcca aaagttggcc    900
cagggcttcc cggtatcaac agggacacca ggatttattt attctgcgaa gtgatcttcc    960
gtcacaggta tttattcggc gcaaagtgcg tcgggtgatg ctgccaactt actgatttag   1020
tgtatgatgg tgttttttgag gtgctccagt ggcttctgtt tctatcagc             1069
```

<210> SEQ ID NO 8
<211> LENGTH: 19
<212> TYPE: DNA
<213> ORGANISM: Artificial Sequence
<220> FEATURE:
<223> OTHER INFORMATION: primer-pMOD<MCS>FP-1

<400> SEQUENCE: 8

```
attcaggctg cgcaactgt                                                  19
```

<210> SEQ ID NO 9
<211> LENGTH: 22
<212> TYPE: DNA
<213> ORGANISM: Artificial Sequence
<220> FEATURE:
<223> OTHER INFORMATION: primer-pMOD<MCS>RP-1

<400> SEQUENCE: 9

```
tcagtgagcg aggaagcgga ag                                              22
```

<210> SEQ ID NO 10
<211> LENGTH: 28
<212> TYPE: DNA
<213> ORGANISM: Artificial Sequence
<220> FEATURE:
<223> OTHER INFORMATION: primer-Tn5Ext

<400> SEQUENCE: 10

```
agcatacatt atacgaagtt atattaag                                        28
```

<210> SEQ ID NO 11

```
<211> LENGTH: 35
<212> TYPE: DNA
<213> ORGANISM: Artificial Sequence
<220> FEATURE:
<223> OTHER INFORMATION: primer-Arb1
<220> FEATURE:
<221> NAME/KEY: misc_feature
<222> LOCATION: (21)..(30)
<223> OTHER INFORMATION: n is a or g or c or t

<400> SEQUENCE: 11
ttgagcgata gacgtacgat nnnnnnnnnn gatat                              35

<210> SEQ ID NO 12
<211> LENGTH: 20
<212> TYPE: DNA
<213> ORGANISM: Artificial Sequence
<220> FEATURE:
<223> OTHER INFORMATION: primer-Arb2

<400> SEQUENCE: 12
ttgagcgata gacgtacgat                                              20

<210> SEQ ID NO 13
<211> LENGTH: 25
<212> TYPE: DNA
<213> ORGANISM: Artificial Sequence
<220> FEATURE:
<223> OTHER INFORMATION: primer-Tn5Int

<400> SEQUENCE: 13
tcgacctgca ggcatgcaag cttca                                        25
```